US009706958B2

(12) United States Patent
Hoke et al.

(10) Patent No.: US 9,706,958 B2
(45) Date of Patent: Jul. 18, 2017

(54) METHODS FOR CHARACTERIZING IN VIVO OPERATIONS OF OBJECTS

(71) Applicant: The Procter & Gamble Company, Cincinnati, OH (US)

(72) Inventors: Phyllis D. Hoke, Loveland, OH (US); Julie Myers Grender, Cincinnati, OH (US); Jill Renee Underwood, Kenwood, OH (US); Gregory John Carr, Wyoming, OH (US); Malgorzata Klukowska, Mason, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 423 days.

(21) Appl. No.: 14/249,733

(22) Filed: Apr. 10, 2014

(65) Prior Publication Data
US 2015/0289806 A1 Oct. 15, 2015

(51) Int. Cl.
*A61C 19/045* (2006.01)
*A61B 5/00* (2006.01)
*A61C 13/225* (2006.01)
*A61B 5/11* (2006.01)

(52) U.S. Cl.
CPC .......... *A61B 5/4851* (2013.01); *A61B 5/1114* (2013.01); *A61C 19/045* (2013.01); *A61B 5/1123* (2013.01); *A61B 5/1126* (2013.01); *A61B 5/4528* (2013.01); *A61B 5/4542* (2013.01); *A61B 5/4547* (2013.01); *A61B 5/682* (2013.01); *A61B 5/7246* (2013.01); *A61B 5/743* (2013.01); *A61C 13/225* (2013.01)

(58) Field of Classification Search
CPC ....... A61C 19/04; A61C 19/045; A61B 5/062; A61B 5/064; A61B 5/065; A61B 5/1111
See application file for complete search history.

(56) References Cited

U.S. PATENT DOCUMENTS 4,342,086 A 7/1982 Adib
4,788,987 A * 12/1988 Nickel ................ A61C 19/045
324/207.15

(Continued)

OTHER PUBLICATIONS

International Search Report and Written Opinion, mail date Aug. 7, 2015, 12 pages.

(Continued)

*Primary Examiner* — Ralph Lewis

(57) ABSTRACT

According to the embodiments described herein, a method for characterizing in vivo operation of a dental prosthetic can include providing subject position data and prosthetic position data. The method may further include transforming the subject position data into a reference three-dimensional coordinate system. The reference three-dimensional coordinate system can be ordered according to a coordinate index. The coordinate index can be based at least in part upon a subject position index of the subject position data. The method may further include comparing, automatically with one or more processors, the prosthetic position data and the reference three-dimensional coordinate system according to a comparison order to characterize the dental prosthetic. The comparison order can be based at least in part upon a prosthetic position index of the prosthetic position data and the coordinate index.

24 Claims, 7 Drawing Sheets

(56) References Cited

U.S. PATENT DOCUMENTS

| | | | | |
|---|---|---|---|---|
| 4,836,778 | A * | 6/1989 | Baumrind | A61C 19/045 356/139.03 |
| 6,621,491 | B1 * | 9/2003 | Baumrind | A61C 7/08 345/419 |
| 7,402,996 | B2 * | 7/2008 | Arai | A61B 5/1126 324/207.11 |
| 8,337,202 | B2 * | 12/2012 | Bando | A61B 5/1121 433/68 |
| 8,801,432 | B2 * | 8/2014 | Kurti, Jr. | A61B 5/742 433/37 |
| 9,125,624 | B2 * | 9/2015 | Dekel | A61B 6/12 |
| 2006/0271199 | A1 * | 11/2006 | Johnson | A61B 5/06 623/18.12 |
| 2007/0264609 | A1 * | 11/2007 | Brunner | A61B 5/1114 433/69 |
| 2011/0053110 | A1 | 3/2011 | Bando et al. | |
| 2014/0248574 | A1 * | 9/2014 | Yoon | A61C 13/01 433/8 |
| 2015/0289960 | A1 | 10/2015 | Shigemoto et al. | |

OTHER PUBLICATIONS

Hasegawa Si et al: "Effect of denture adhesive on stability of complete dentures and the masticatory function". Journal of Medical and Dental Sciences. vol. 50, No. 4, Dec. 2003 (Dec. 2003), pp. 239-247, XP055204292. JP ISSN: 1342-8810.

Grasso J et al: "Effect of denture adhesive on retention of the mandibular and maxillary dentures during function". Journal of Clinical Dentistry, Professional Audience Communications. Yardley. PA. US. vol. 11. No. 4, Jan. 2000 (Jan. 2000). pp. 98-103. XP009185519, ISSN: 0895-8831.

Bonaventura P et al: "Assessment of speech production with dentures by electromagnetic articulography", The Effect of Applied Compressive Loading on Tissue-Engineered Cartilage Constructs Cultured With TGF-BETA3. IEEE, Jul. 3, 2013 (Jul. 3, 2013), pp. 4710-4713, XP032488419, ISSN: 1557-170X. DOI: 10.1109/EMBC.2013.6610599 [retrieved on Sep. 25, 2013].

* cited by examiner

METHODS FOR CHARACTERIZING IN VIVO OPERATIONS OF OBJECTS

BACKGROUND OF THE INVENTION

The present specification generally relates to methods for characterizing operations of objects and, more specifically, to methods for characterizing in vivo operations of dental prosthesis.

Dental prosthesis such as, for example, dentures can be worn within the oral cavity of users to replace missing teeth. The dentures can be supported within the oral cavity by topography formed by soft and hard tissues of the oral cavity. Due to geometrical differences between users, expert care may be required to form the dentures to match the oral cavity in order to promote support, stability, and retention. However, even with expert care, a properly fitted denture still may experience periods of reduced support, stability, and retention during typical use like chewing or talking. Denture adhesive can be utilized to improve the support, stability, and retention of the dentures.

Measuring the efficacy of the dentures, the denture adhesive, or both during typical use can be a difficult task. Known measurement techniques can be complicated due to the intrusive nature of working with the oral cavity of the users. Moreover, known measurement techniques have relied upon external rigging that can create inertial artifacts within the measurement data. Alternative techniques have relied upon detectors that fail to produce data sufficient to characterize the dentures during typical use. Moreover, the efficacy of anecdotal data from users can be reduced due to the varied experience of each user and the prevalence of improperly fitting dentures.

Accordingly, a need exists for alternative methods for characterizing in vivo operations of dental prosthesis.

SUMMARY OF THE INVENTION

In one embodiment, a method for characterizing in vivo operation of a dental prosthetic can include providing subject position data. The subject position data can be derived from subject position signals transmitted by one or more subject position sensors attached to a measurement subject. The subject position data can be ordered according to a subject position index. The method may further include providing prosthetic position data. The prosthetic position data can be derived from prosthetic tracking signals transmitted by one or more prosthetic tracking sensors attached to the dental prosthetic located within an oral cavity of the measurement subject. The one or more prosthetic tracking sensors can be non-line-of-sight sensors. The prosthetic tracking signals and the subject position signals can be transmitted contemporaneously. The prosthetic position data can be ordered according to a prosthetic position index. The method may further include transforming the subject position data into a reference three-dimensional coordinate system. The reference three-dimensional coordinate system can be ordered according to a coordinate index. The coordinate index can be based at least in part upon the subject position index. The method may further include comparing, automatically with one or more processors, the prosthetic position data and the reference three-dimensional coordinate system according to a comparison order to characterize the dental prosthetic. The comparison order can be based at least in part upon the prosthetic position index and the coordinate index.

In another embodiment, a method for characterizing in vivo operation of a dental prosthetic can include providing subject position data. The subject position data can be derived from subject position signals transmitted by one or more subject position sensors attached to a measurement subject. The subject position data can be ordered according to a subject position index. The method may further include providing prosthetic position data. The prosthetic position data can be derived from prosthetic tracking signals transmitted by one or more prosthetic tracking sensors attached to the dental prosthetic located within an oral cavity of the measurement subject. The one or more prosthetic tracking sensors can be reactive to an excitation field. The prosthetic tracking signals and the subject position signals can be transmitted contemporaneously. The prosthetic position data can be ordered according to a prosthetic position index. The method may further include transforming the subject position data into a reference three-dimensional coordinate system. The reference three-dimensional coordinate system can be ordered according to a coordinate index. The coordinate index can be based at least in part upon the subject position index. The method may further include comparing, automatically with one or more processors, the prosthetic position data and the reference three-dimensional coordinate system according to a comparison order to characterize the dental prosthetic. The comparison order can be based at least in part upon the prosthetic position index and the coordinate index.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
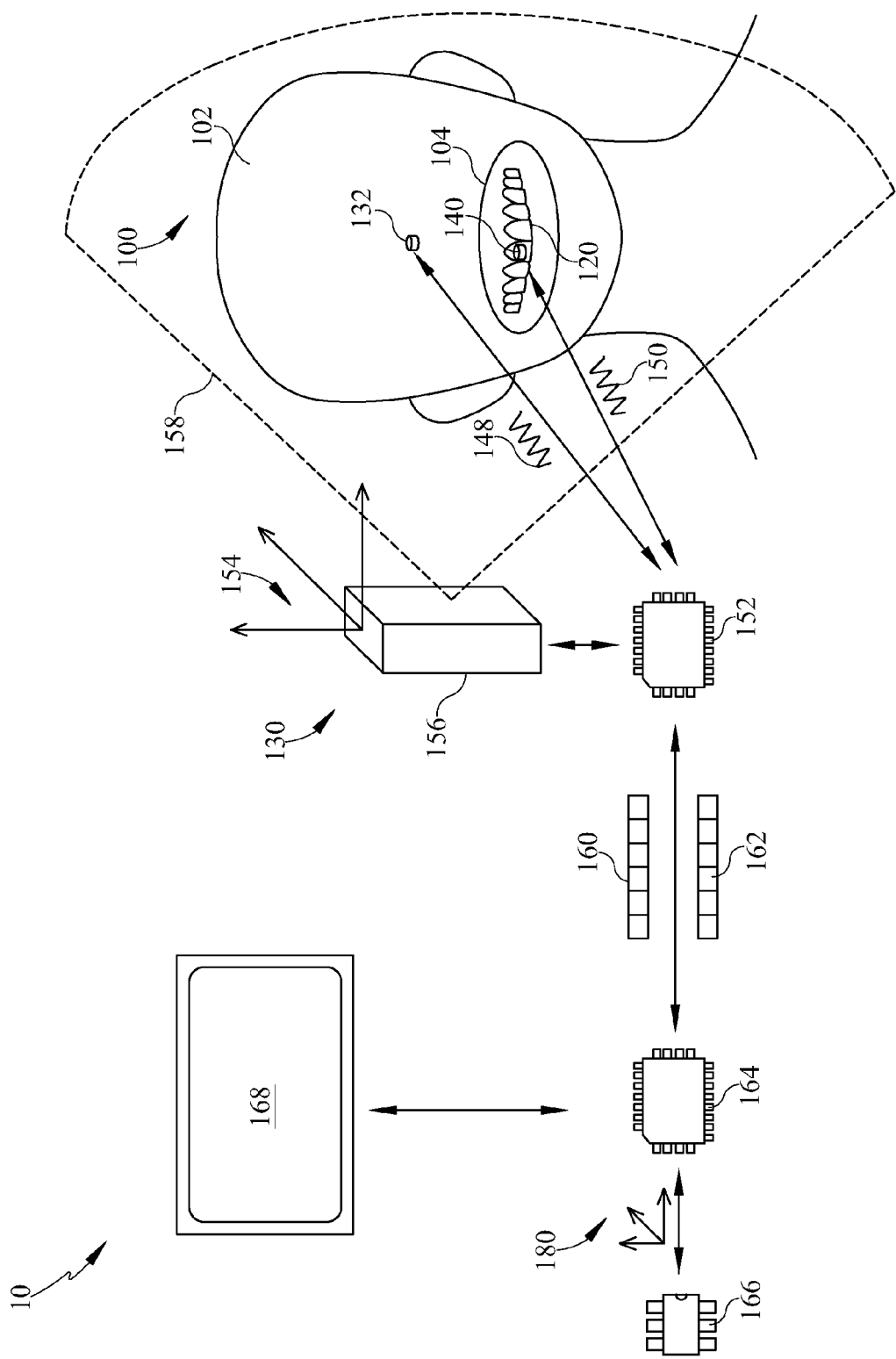
FIG. 1 schematically depicts a system for characterizing in vivo operations of dental prosthesis according to one or more embodiments shown and described herein.
Figure 3:
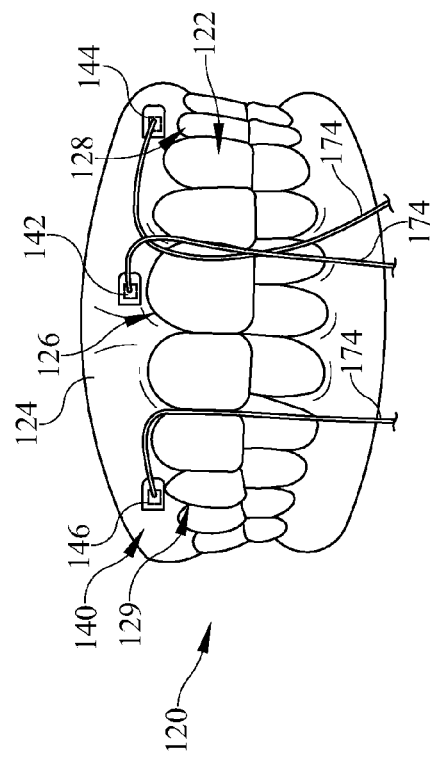
FIG. 3 schematically depicts a dental prosthetic according to one or more embodiments shown and described herein.
Figure 2A:
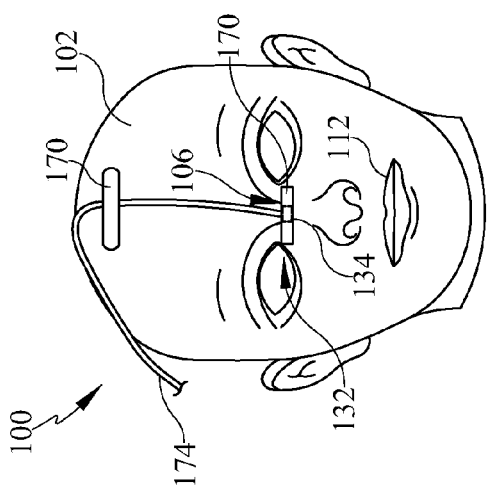
FIGS. 2A and 2B schematically depict a head of a measurement subject according to one or more embodiments shown and described herein.
Figure 2B:
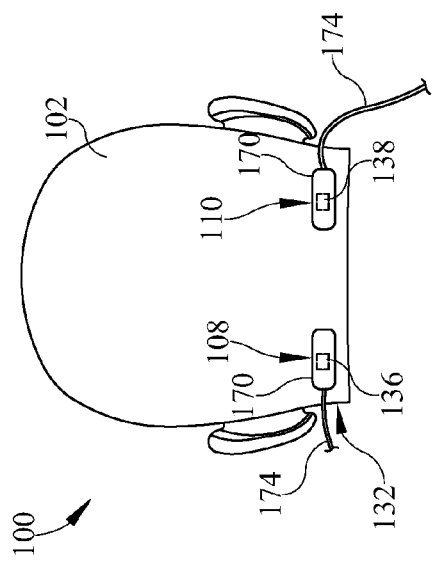

Referring to FIG. 1, the embodiments described herein relate to capturing and communicating in vivo data, i.e., data that is indicative of characteristics of objects worn or placed within a measurement subject 100 under typical use. Accordingly, the observed characteristics of the objects can be illustrative of the interaction between the measurement subject 100 and the objects such as, for example, medical devices, wearable devices, or the like. As is described in greater detail herein, the observed characteristics can be utilized for design, development, demonstration, evaluation, or the like. In some embodiments, the interaction between the measurement subject 100 and a dental prosthetic 120 can be observed. Thus, the measurement subject 100 can be human and, thus, can comprise a head 102 and an oral cavity 104. It is noted that the observed characteristics can be collected by taking a significant number of samples of one or more measurement subject 100.

The dental prosthetic 120 can be any type of device that is wearable within the oral cavity 104 of the measurement subject 100 such as, for example, dentures or false teeth. For example, the dental prosthetic 120 can be configured as a complete denture that can be worn to replace missing teeth. It is noted that, while the dental prosthetic 120 is depicted in FIG. 1 as a maxillary denture, the dental prosthetic 120 can be configured as a full or partial maxillary denture, a full or partial mandibular denture, or combinations thereof. The dental prosthetic 120 can comprise one or more teeth 122 and a retention surface 124 configured to attach the dental prosthetic 120 to the oral mucosa of the oral cavity 104 of the measurement subject 100. Specifically, the retention surface 124 can be formed or molded to match the topography of the oral cavity 104. Accordingly, the dental prosthetic 120 can be attached to the oral cavity 104 with the retention surface 124 via, for example, surface tension or denture adhesive. The dental prosthetic 120 can be formed out of a substantially rigid material such as, for example, a clear or colored acrylic, or any other moldable material.

Spatial Positioning System

The measurement subject 100 and the dental prosthetic 120 can be observed with a spatial positioning system 130. During such observation, the measurement subject can perform various tasks consistent with typical use, e.g., chewing, speaking, kissing, whistling, playing instruments, or the like. The spatial positioning system 130 can comprise any type of motion capture system suitable for capturing measurements of the interaction between the measurement subject 100 and the dental prosthetic 120. In some embodiments, the spatial positioning system 130 can comprise a non-line-of-sight motion capture system. Exemplary non-line-of-sight motion capture systems include, but are not limited to, the Wave system by Northern Digital Inc. of Waterloo, Ontario, Canada and the Articulograph AG500 by Carstens Medizinelektronik GmbH of Bovenden, Germany.

The spatial positioning system 130 can comprise one or more subject position sensors 132 that transform characteristics of the measurement subject 100 into subject position signals 148 and one or more prosthetic tracking sensors 140 that transform characteristics of the dental prosthetic 120 into prosthetic tracking signals 150. As used herein, the term "signal" can mean a waveform (e.g., electrical, optical, magnetic, or electromagnetic), such as DC, AC, sinusoidal-wave, triangular-wave, square-wave, or the like, capable of propagating via a medium. The subject position signals 148 and the prosthetic tracking signals 150 can provide positional data at data rate that is high enough to capture motion of the measurement subject 100 and the dental prosthetic 120 during tasks consistent with typical use. In some embodiments, the data rate can be greater than about 100 measurements per second.

The spatial positioning system 130 can comprise one or more spatial processors 152 for automatically performing data processing functions. The data processing functions can comprise establishing a spatial coordinate system 154. Specifically, the spatial coordinate system 154 can establish a three-dimensional coordinate system such as, for example, a cartesian coordinate system, a polar coordinate system, or the like. The spatial coordinate system 154 can be utilized within the data processing functions to link the subject position signals 148 and the prosthetic tracking signals 150. Accordingly, the positional data of the subject position signals 148 and the prosthetic tracking signals 150 can be associated with and can be defined relative to the spatial coordinate system 154.

Referring still to FIG. 1, the spatial positioning system 130 can comprise a field generator 156 for generating fields that can be transformed by the one or more subject position sensors 132 into subject position signals 148 and the one or more prosthetic tracking sensors 140 into prosthetic tracking signals 150. For example, the field generator 156 can generate an excitation field 158 that can comprise one or more electromagnetic field, electrical field, magnetic field or the like. In one embodiment, the excitation field 158 can comprise a sequence or set of magnetic fields.

Accordingly, each of the one or more subject position sensors 132 and the one or more prosthetic tracking sensors 140 can be configured to be reactive to the sequence or set of magnetic fields. Specifically, in some embodiments, each of the one or more subject position sensors 132 and the one or more prosthetic tracking sensors 140 can comprise a coil that is reactive to the excitation field 158. In embodiments where the field generator 156 generates an excitation field 158 comprising a plurality of different spatial magnetic field shapes, or distributions, each of the one or more subject position sensors 132 and the one or more prosthetic tracking sensors 140 can produce signals dependent upon each of the different fields. Accordingly, the subject position signals 148 can be indicative of the pose of each of the one or more subject position sensors 132. Similarly, the prosthetic tracking signals 150 can be indicative of the pose of each of the one or more prosthetic tracking sensors 140. For the purpose of defining and describing the present disclosure, the term "pose," as used herein, can mean the position, orientation, or both of an object. Furthermore, it is noted that each of the one or more subject position sensors 132 and the one or more prosthetic tracking sensors 140 can be non-line-of-sight motion sensors, i.e., the sensors can be configured to operate with visual obstructions blocking a direct path between the sensors and a source of excitation or the sensors and an object communicatively coupled with the sensors.

The data processing functions can comprise transforming the subject position signals 148 into subject position data 160 indicative of the pose of each of the one or more subject position sensors 132 with respect to the spatial coordinate system 154. Additionally, the data processing functions can comprise transforming the prosthetic tracking signals 150 into prosthetic position data 162 indicative of the pose of each of the one or more prosthetic tracking sensors 140 with respect to the spatial coordinate system 154.

According to the embodiments described herein, one or more comparison processors 164 can be provided for automatically executing comparison functions with the subject position data 160 and the prosthetic position data 162. In some embodiments, the one or more comparison processors 164 can be communicatively coupled to comparison memory 166. In some embodiments, the subject position data 160 and the prosthetic position data 162 can be stored on the comparison memory 166 and accessed by the one or more comparison processors while executing comparison functions. Alternatively or additionally, the one or more comparison processors 164 or the comparison memory 166 can be communicatively coupled to the one or more spatial processors 152 such that the subject position data 160 and the prosthetic position data 162 is communicated from the spatial positioning system 130 to the one or more comparison processors 164 or the comparison memory 166.

In some embodiments, a display 168 for emitting optical signals to present output of the comparison functions as images can be communicatively coupled to the one or more comparison processors 164, the comparison memory 166, or both. The display 168 can comprise any medium capable of transmitting an optical output such as, for example, a cathode ray tube, light emitting diodes, liquid crystal displays, plasma displays, or the like. As used herein, the phrase "communicatively coupled" can mean that components are capable of exchanging data signals with one another such as, for example, electrical signals via conductive medium, electromagnetic signals via air, optical signals via optical waveguides, and the like.

For the purpose of defining and describing the present disclosure, it is noted that the term "processor" generally means a device that executes functions according to machine readable instructions such as, for example, an integrated circuit, a microchip, a computer, a central processing unit, a graphics processing unit, field-programmable gate array (FPGA), an application-specific integrated circuit (ASIC), or any other computation device. Additionally, it is noted that the term "memory," as used herein, generally means one or more apparatus capable of storing data or machine readable instructions for later retrieval such as, but not limited to, RAM, ROM, flash memory, hard drives, or combinations thereof.

It is furthermore noted that the machine readable instructions described herein may comprise logic or algorithms written in any programming language of any generation (e.g., 1GL, 2GL, 3GL, 4GL, or 5GL) such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the logic or algorithm may be written in a hardware description language (HDL), such as implemented via either an FPGA configuration or an ASIC, or their equivalents.

System

Referring collectively to FIGS. 1, 2A, 2B, and 3, an embodiment of a system 10 for characterizing in vivo operation of the dental prosthetic 120 is schematically depicted. The system 10 can comprise a spatial positioning system 130 comprising the one or more subject position sensors 132 attached to the head 102 of the measurement subject 100 and the one or more prosthetic tracking sensors 140 attached to the dental prosthetic 120. In one embodiment, the one or more subject position sensors 132 can comprise a first subject position sensor 134, a second subject position sensor 136, and a third subject position sensor 138. The first subject position sensor 134, the second subject position sensor 136, and the third subject position sensor 138 can be arranged around the head 102 of the measurement subject 100 in a substantially triangular pattern. For example, each of the first subject position sensor 134, the second subject position sensor 136, and the third subject position sensor 138 can define a vertex of the substantially triangular pattern of the one or more subject position sensors 132. The first subject position sensor 134 can be attached to the bridge of the nose 106 of the head 102 of the measurement subject 100. The second subject position sensor 136 can be attached to the left mastoid 108 of the head 102 of the measurement subject 100. The third subject position sensor 138 can be attached to the right mastoid 110 of the head 102 of the measurement subject 100. In some embodiments, each of the one or more subject position sensors 132 can be oriented to face substantially the same direction.

The applicants have discovered that the one or more subject position sensors 132 can be reused when the one or more subject position sensors 132 are attached to the measurement subject 100 with a temporary attachment 170. The temporary attachment 170 can comprise a flexible material layer and an adhesive layer. Suitable temporary attachments include an adhesive bandage such as, for example, Tegaderm™ by 3M™ of St. Paul, Minn., U.S.A., or the like. Accordingly, the one or more subject position sensors 132 can be directly attached to the head 102 of the measurement subject 100.

In one embodiment, the one or more prosthetic tracking sensors 140 can comprise a first prosthetic tracking sensor 142, a second prosthetic tracking sensor 144, and a third prosthetic tracking sensor 146. The first prosthetic tracking sensor 142, the second prosthetic tracking sensor 144, and the third prosthetic tracking sensor 146 can be arranged around the dental prosthetic 120 in a substantially triangular pattern. For example, each of the first prosthetic tracking sensor 142, the second prosthetic tracking sensor 144, and the third prosthetic tracking sensor 146 can define a vertex of the substantially triangular pattern of the one or more prosthetic tracking sensors 140. The first prosthetic tracking sensor 142 can be attached to a central incisor 126 of the dental prosthetic 120. The second prosthetic tracking sensor 144 can be attached to the dental prosthetic 120 at a medial of a left second pre-molar 128. The third prosthetic tracking sensor 146 can be attached to the dental prosthetic 120 at a medial of a right second pre-molar 129. In some embodiments, the substantially triangular pattern of the one or more prosthetic tracking sensors 140 can define a smaller perimeter than the substantially triangular pattern of the one or more subject position sensors 132.

In some embodiments, the one or more prosthetic tracking sensors 140 can be embedded into the dental prosthetic 120. Specifically, the dental prosthetic 120 can be drilled to form a hole for accepting each of the one or more prosthetic tracking sensors 140, i.e., drilled to accommodate the outer dimensions of the sensor. For example, each of the one or more prosthetic tracking sensors 140 can comprise a substantially square shaped cross-section, the holes can have a depth, a width, and a height that is large enough to accept each of the one or more prosthetic tracking sensors 140. The holes can further comprise a channel to accept a portion of a wire 174 of accept each of the one or more prosthetic tracking sensors 140. For example, the channel can have a length from about 2 mm to about 10 mm. Once placed in a hole with the wire 174 arranged within the channel, acrylic or dental wax can be applied to cover the sensor to embed the sensor within the dental prosthetic 120. Thus, the wires 174, when present, of the one or more prosthetic tracking sensors 140 can be configured to exit the oral cavity 104 via the corners of the mouth 112 of the measurement subject 100. In some embodiments, the acrylic or dental wax can be colored to contrast with the color of the dental prosthetic 120. Accordingly, should the one of the one or more prosthetic tracking sensors 140 malfunction, the contrasting colored acrylic or dental wax can be removed to facilitate removal and replacement.

Referring still to FIGS. 1, 2A, 2B, and 3, the spatial positioning system 130 can comprise one or more spatial processors 152 communicatively coupled to the first subject position sensor 134, the second subject position sensor 136, the third subject position sensor 138, the first prosthetic tracking sensor 142, the second prosthetic tracking sensor 144, and the third prosthetic tracking sensor 146. The measurement subject 100 can be located within range of the excitation field 158 of the field generator 156 of the spatial positioning system. Specifically, the first subject position sensor 134, the second subject position sensor 136, the third subject position sensor 138, the first prosthetic tracking sensor 142, the second prosthetic tracking sensor 144, and the third prosthetic tracking sensor 146 can be within range of the excitation field 158. Additionally, the one or more spatial processors 152 can receive the subject position signals 148 and the prosthetic tracking signals 150. For example, the wires 174 of the first subject position sensor 134, the second subject position sensor 136, and the third subject position sensor 138 can transmit the subject position signals 148 to the one or more spatial processors 152. Similarly, the wires 174 of the first prosthetic tracking sensor 142, the second prosthetic tracking sensor 144, and the third prosthetic tracking sensor 146 can transmit the prosthetic tracking signals 150 to the one or more spatial processors 152.

The spatial positioning system 130 can comprise the field generator 156 communicatively coupled to the one or more spatial processors 152. Accordingly, the one or more spatial processors 152 can execute data processing functions to control the operation of the field generator 156. Additionally, the one or more spatial processors 152 can execute data processing functions to transform the subject position signals 148 into the subject position data 160. The one or more spatial processors 152 can execute data processing functions to transform the prosthetic tracking signals 150 into the prosthetic position data 162.

In some embodiments, the system 10 for characterizing in vivo operation of the dental prosthetic 120 can comprise one or more comparison processors 164 communicatively coupled to the spatial positioning system 130. The one or more comparison processors 164 can be communicatively coupled to the comparison memory 166 and the display 168. Accordingly, the subject position data 160 and the prosthetic position data 162 can be provided to the one or more comparison processors 164 for executing display functions. Alternatively or additionally, the subject position data 160 and the prosthetic position data 162 can be provided after being stored in the comparison memory 166.

In addition to the embodiments of the system 10 depicted in FIG. 1, the embodiments described herein comprise further embodiments for performing display functions with the subject position data 160 and the prosthetic position data 162. In some embodiments, the subject position data 160 and the prosthetic position data 162 can be stored to the comparison memory 166 without the one or more comparison processors 164 being communicatively coupled to the spatial positioning system 130. For example, the comparison memory 166 can comprise portable memory (e.g., flash drive or disk) that can be loaded with the subject position data 160 and the prosthetic position data 162. Additionally, it is noted that each of the one or more comparison processors 164 and the comparison memory 166 may be a discrete components communicatively coupled with one another without departing from the scope of the present disclosure. For example, a server client relationship can be established to distribute the subject position data 160 and the prosthetic position data 162 from the spatial positioning system 130 to a variety of client devices each with processors, memory, and displays such that each client device can perform the display functions. It is furthermore noted that, while the one or more spatial processors 152 and the one or more comparison processors 164 are depicted in FIG. 1 as separate entities, the one or more spatial processors 152 and the one or more comparison processors 164 can be integral. Moreover, it is noted that the one or more spatial processors 152 can perform at least some of the display functions and the one or more comparison processors 164 can perform at least some of the data processing functions without departing from the scope of the present disclosure.

Referring again to FIGS. 1, 2A, 2B, and 3, embodiments of the present disclosure can be utilized to characterize in vivo operation of the dental prosthetic 120. For example, the spatial positioning system 130 can be utilized to collect a significant number of samples of in vivo operation. One or more samples can be collected using one or more test subjects. An exemplary method for collecting samples from the measurement subject 100 is provided below. It is noted that, while system 10 is depicted in FIG. 1 as having only the measurement subject 100, data may be collected from a large population of people.

Test Setup

The measurement subject 100 can be an individual having a full or partial set of dentures that have been customized to fit accurately within the oral cavity 104 of the measurement subject 100. The dental prosthetic 120 can be formed to substantially duplicate the dentures, i.e., the dental prosthetic 120 for use in testing can replicate the dentures of the measurement subject 100. Once the dental prosthetic 120 has been created, the one or more prosthetic tracking sensors 140 can be attached to the dental prosthetic 120.

The dental prosthetic 120 can be sterilized and prepared according to a typical use scenario. As is described in greater detail herein, the dental prosthetic 120 can have a variety of different types of denture adhesive applied to the retention surface 124. In some embodiments, comparison evaluations between different types of denture adhesive can be performed. Accordingly, it may be desirable to apply a standard dosage of denture adhesive during preparation for the typical use scenario. Alternatively or additionally, the denture adhesives can be applied according to manufacturers' directives. In the alternative, the dental prosthetic 120 can be prepared according to a typical use scenario without applying denture adhesive to the retention surface 124.

The measurement subject 100 may be prepared for testing according to one or more protocols. In some embodiments, the measurement subject 100 may abstain from the use of denture adhesive for a predetermined period of time prior to the measurement. After the predetermined time period has expired, the dental prosthetic 120 can be introduced into the oral cavity 104 of the measurement subject 100. Alternatively or additionally, the oral cavity 104 of the measurement subject can be inspected and cleaned to remove any undesired substances prior to attaching the dental prosthetic 120 to the measurement subject 100.

In some embodiments, the one or more subject position sensors 132 can be attached to the head 102 of the measurement subject 100 after the dental prosthetic 120 has been attached to the oral cavity 104. As is noted above, the one or more subject position sensors 132 can be attached using the temporary attachment 170. The head 102 of the measurement subject 100 can be cleaned prior to attaching the one or more subject position sensors 132. For example, prior to applying the temporary attachment 170, the skin of the measurement subject can be cleaned with an alcohol solution.

Collect Data

Referring again to FIG. 1, as is noted above, the one or more subject position sensors 132 can be attached to the measurement subject 100 and the one or more prosthetic tracking sensors 140 can be embedded within the dental prosthetic 120 that is located within the oral cavity 104 of the measurement subject 100. The measurement subject 100 can be oriented with respect to the spatial positioning system 130 such that the one or more subject position sensors 132 and the one or more prosthetic tracking sensors 140 are within the excitation field 158. The measurement subject 100 can maintain a rest position for a predetermined resting time period while the spatial positioning system 130 collects data. In some embodiments, the rest position can comprise maintaining a substantially fixed position. Specifically, the one or more subject position sensors 132 can interact with the excitation field generated 158 of the field generator 156 to generate the subject position signals 148 indicative of the head 102 of the measurement subject 100 in the rest position during the resting time period. Similarly, the one or more prosthetic tracking sensors 140 can interact with the excitation field 158 generated by the field generator 156 to generate the prosthetic tracking signals 150 indicative of the dental prosthetic 120 within the oral cavity 104 of the measurement subject 100 in the rest position during the resting time period. In some embodiments, the subject position signals 148 indicative of the rest position and the prosthetic tracking signals 150 indicative of the rest position can be transmitted to and received by the one or more spatial processors 152 throughout the resting time period.

Alternatively or additionally, the measurement subject 100 can perform one or more tasks consistent with typical use for a predetermined usage time period while the spatial positioning system 130 collects data. Specifically, the one or more subject position sensors 132 can interact with the excitation field generated 158 of the field generator 156 to generate the subject position signals 148 indicative of movement of the head 102 of the measurement subject 100 during the one or more tasks consistent with typical use. Similarly, the one or more prosthetic tracking sensors 140 can interact with the excitation field 158 generated by the field generator 156 to generate the prosthetic tracking signals 150 indicative of movement of the dental prosthetic 120 within the oral cavity 104 of the measurement subject 100 during the one or more tasks consistent with typical use. In some embodiments, the subject position signals 148 indicative of movement of the head 102 of the measurement subject 100 and the prosthetic tracking signals 150 indicative of movement of the dental prosthetic 120 within the oral cavity 104 of the measurement subject 100 can be transmitted to and received by the one or more spatial processors 152 throughout the usage time period.

As is noted above, the measurement subject 100 can perform various tasks consistent with typical use during the usage time period. In some embodiments, the tasks consistent with typical use can comprise a gum chewing activity. Specifically, the measurement subject 100 can chew gum as the subject position signals 148 are transmitted by the one or more subject position sensors 132 and the prosthetic tracking signals 150 are transmitted by the one or more prosthetic tracking sensors 140. Alternatively or additionally, the tasks consistent with typical use can comprise a reading aloud activity. Specifically, the measurement subject 100 can read aloud a predetermined passage as the subject position signals 148 are transmitted by the one or more subject position sensors 132 and the prosthetic tracking signals 150 are transmitted by the one or more prosthetic tracking sensors 140. Alternatively or additionally, the tasks consistent with typical use can comprise a tongue twister activity. Specifically, the measurement subject 100 can utter tongue twisters, i.e., one or more phrase designed to be difficult to articulate properly, as the subject position signals 148 are transmitted by the one or more subject position sensors 132 and the prosthetic tracking signals 150 are transmitted by the one or more prosthetic tracking sensors 140.

In some embodiments, the spatial positioning system 130 can collect data indicative of the rest position prior to collecting data indicative of the one or more tasks consistent with typical use. Optionally, replicates of data indicative of the rest position, data indicative of the one or more tasks consistent with typical use, or both can be collected with during a single testing instance. In one embodiment, during the single test instance, the measurement subject 100 can maintain the rest position, perform a first task consistent with typical use, maintain the rest position, perform a second task consistent with typical use, maintain the rest position, perform a third task consistent with typical use, and repeat for multiple replicates. Specifically, the measurement subject 100 can perform three of the tasks consistent with typical use (e.g., gum chewing activity, reading aloud activity, tongue twister activity), for about 30 seconds each, i.e., about 10 seconds of the rest position, which can yield about 1,000 measurements, and about 20 seconds of the task consistent with typical use, which can yield about 2,000 measurements. Furthermore, it is noted that populations of data can be generated by collecting data from multiple measurement subjects performing the single test instance or variations thereof.

The tasks consistent with typical use can be designed to characterize the in vivo operation of the dental prosthetic 120. Such characterization can comprise evaluating the efficacy of a denture adhesive. For example, the performance of the dental prosthetic 120 with a denture adhesive can be compared to the performance of the dental prosthetic 120 without the denture adhesive. The applicants have unexpectedly discovered that the gum chewing activity proved capable of generating statistically significant results for the comparison between the performance of the dental prosthetic 120 with the denture adhesive and the performance of the dental prosthetic 120 without the denture adhesive. Alternatively or additionally, the performance of the dental prosthetic 120 with a first denture adhesive can be compared to the performance of the dental prosthetic 120 with a second denture adhesive. The applicants have unexpectedly discovered that the reading aloud activity proved capable of generating statistically significant results for the comparison between the performance of the dental prosthetic 120 with the first denture adhesive and the performance of the dental prosthetic 120 with the second denture adhesive.

Create Reference Coordinate System

Figure 4:
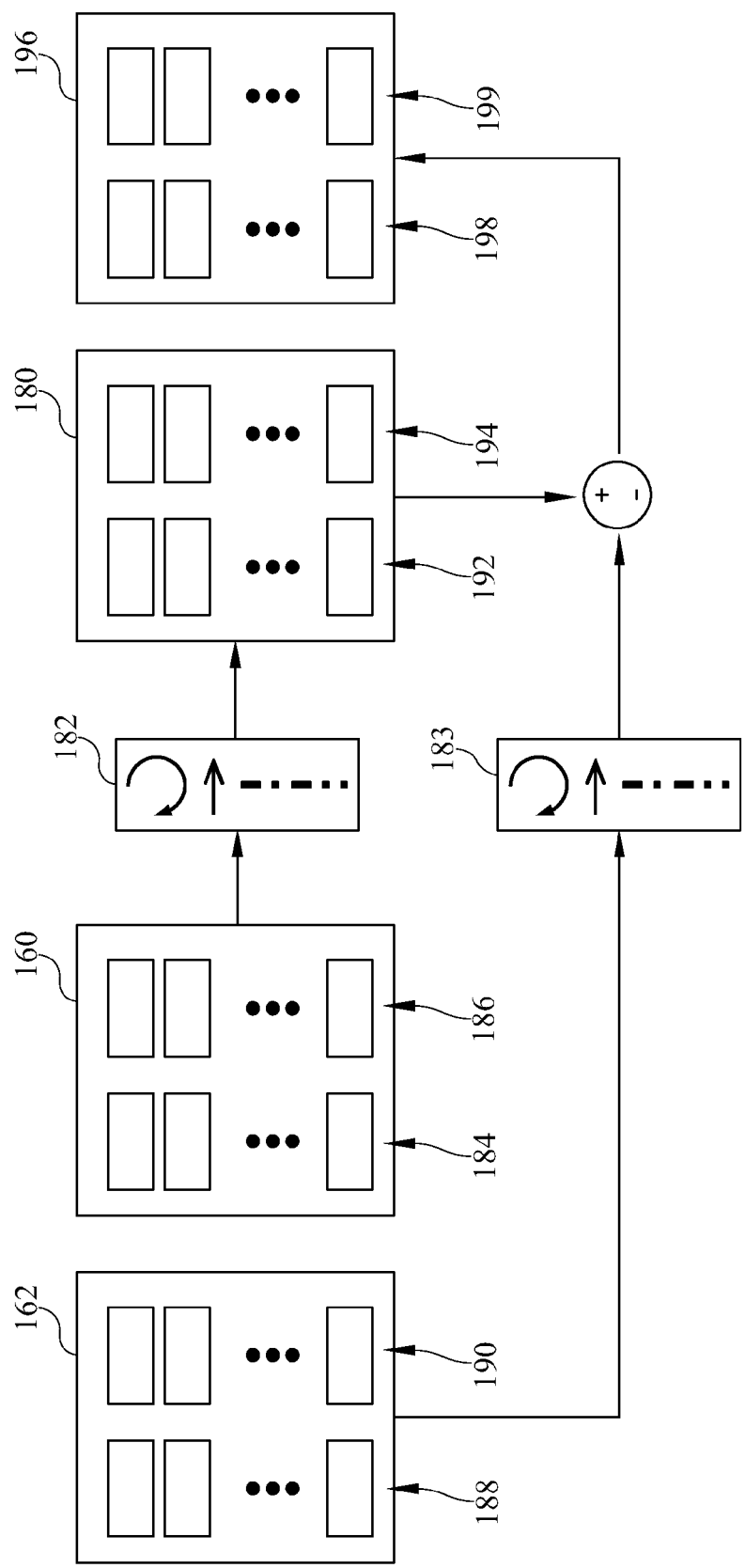
FIG. 4 schematically depicts data transformations according to one or more embodiments shown and described herein.

Referring collectively to FIGS. 1 and 4, the spatial positioning system 130 can derive the subject position data 160 from the subject position signals 148 such that the subject position data 160 is indicative of the positioning of the one or more subject position sensors 132 with respect to the spatial coordinate system 154. In some embodiments, the subject position data 160 can comprise multiple instances of data 184 ordered according to a subject position index 186.

As used herein, the term "index" can mean an attribute associated with data that allows a processor to organize multiple instances of data. As is noted above, the subject position signals 148 can be collected over time, i.e., throughout the resting time period and the usage time period. Accordingly, the subject position signals 148 can include a plurality of measurements. Each of the measurements can be organized in manner indicative of the point in time that the measurement was created such as, for example, according to time of transmission by the one or subject position sensors 132, according to time of receipt by the one or more spatial processors 152, according to order of transmission by the one or subject position sensors 132, according to order of receipt by the one or more spatial processors 152, or the like. The subject position index 186 can be encoded to link the multiple instances of data 184 of the subject position data 160 with the measurements of the subject position signals 148. Thus, the subject position data 160 can be organized in a manner analogous to the organization of the measurements of the subject position signals 148.

Similarly, the spatial positioning system 130 can derive the prosthetic position data 162 from the prosthetic tracking signals 150 such that the prosthetic position data 162 is indicative of the positioning of the one or more prosthetic tracking sensors 140 with respect to the spatial coordinate system 154. In some embodiments, the prosthetic position data 162 can comprise multiple instances of data 188 ordered according to a prosthetic position index 190. Like the subject position signals 148, the prosthetic tracking signals 150 can be collected over time, i.e., throughout the resting time period and the usage time period. Accordingly, the prosthetic tracking signals 150 can include a plurality of measurements indicative of the position of the head 102 of the measurement subject 100. Each of the measurements can be organized in a manner indicative of the point in time that the measurement was created such as, for example, according to time of transmission by the one or more prosthetic tracking sensors 140, according to time of receipt by the one or more spatial processors 152, according to order of transmission by the one or more prosthetic tracking sensors 140, according to order of receipt by the one or more spatial processors 152, or the like. The prosthetic position index 190 can be encoded to link the multiple instances of data 188 of the prosthetic position data 162 with the measurements of the prosthetic tracking signals 150. Thus, the prosthetic position data 162 can be organized in a manner analogous to the organization of the measurements of the prosthetic tracking signals 150.

Figure 5:
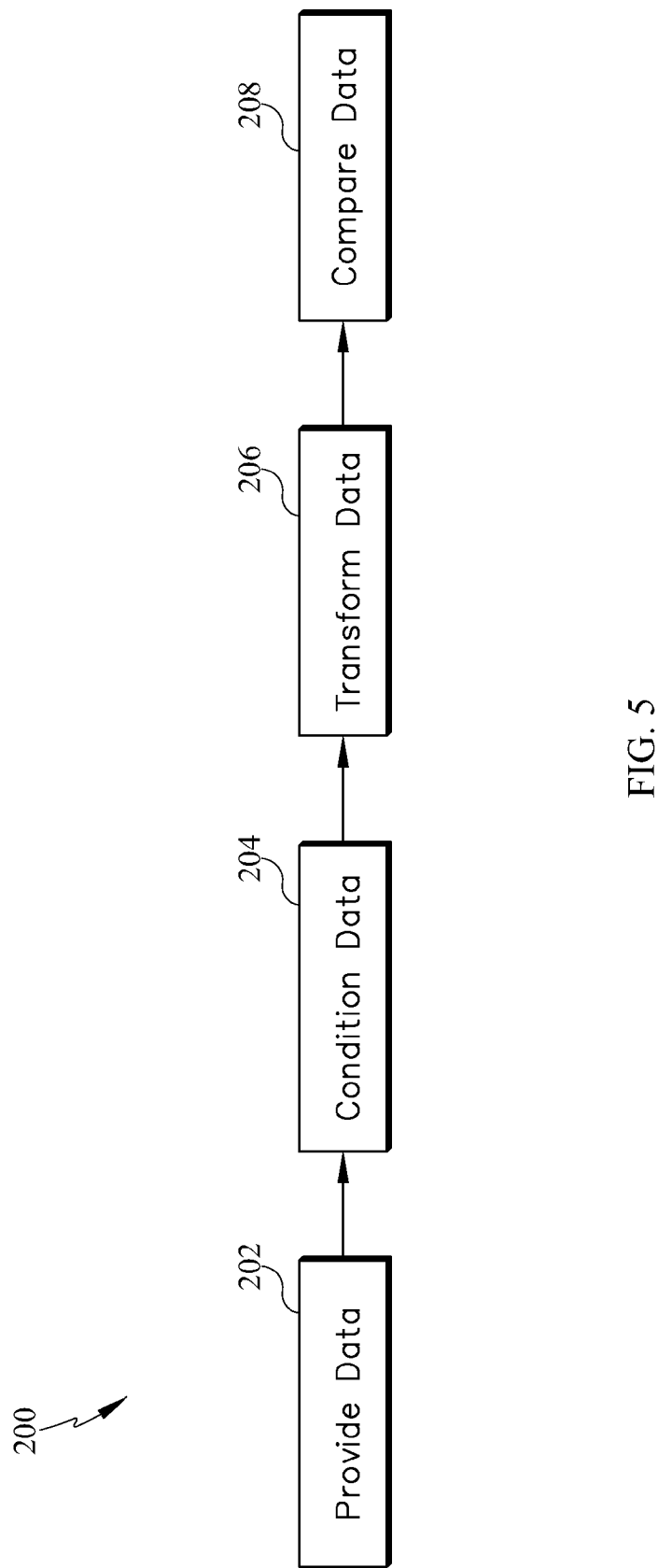
FIG. 5 schematically depicts a method for characterizing in vivo operations of dental prosthesis according to one or more embodiments shown and described herein.

Referring collectively to FIGS. 1 and 5, embodiments of a method 200 for characterizing in vivo operation of the dental prosthetic 120 is schematically depicted. It is noted that, while the method 200 comprises enumerated processes, the processes may be performed in any order without departing from the scope of the present disclosure. Furthermore, it is noted that any of the processes of the method 200 can be omitted without departing from the scope of the present disclosure. At process 202, the subject position data 160 and the prosthetic position data 162 can be provided to the one or more comparison processors 164.

At process 204, the subject position data 160, the prosthetic position data 162, or both can be conditioned for further processing. Specifically, the one or more comparison processors 164 can automatically execute data processing functions such as, for example, regression modeling, filtering, or the like. In some embodiments, the subject position data 160 and the prosthetic position data 162 can have noise or undesired variation. Accordingly, the data can be conditioned to remove the noise or undesired variation. In further embodiments, the subject position data 160 and the prosthetic position data 162 can be "smoothed" by using a Local Regression (LOESS) or Locally Weighted Scatterplot Smoothings (LOWESS). Specifically, measurements sampled at a rate of about 100 samples per second can be smoothed with LOESS using a bandwidth of about 40 consecutive measurements, which is about 1.3% of an about 30 second testing instance. Data in the middle of the bandwidth can be weighted more than the data on the edges of the bandwidth during the smoothing process.

Referring collectively to FIGS. 1, 4 and 5, at process 206, the subject position data 160, the prosthetic position data 162, or both can be subjected to coordinate transformations. In some embodiments, the subject position data 160 can be transformed into a reference three-dimensional coordinate system 180. As is explained in greater detail below, the reference three-dimensional coordinate system 180 can be utilized to characterize the three-dimensional motion of the dental prosthetic 120 relative to the oral cavity 104 of the measurement subject 100. In some embodiments, the reference three-dimensional coordinate system 180 can be utilized to remove undesired motion and artifacts from the prosthetic position data 162. As used herein, the phrase "reference three-dimensional coordinate system" can mean a system that maps elements to a topological space having at least three-dimensions, such that the system is representative of the subject position data 160 with motion of the head 102 of the measurement subject 100 substantially removed.

As is noted above, the reference three-dimensional coordinate system 180 can be derived from the subject position data 160. Accordingly, the coordinate index 194 can be based at least in part upon the subject position index 186. The coordinate index 194 can be encoded to link the multiple instances of data 192 of the reference three-dimensional coordinate system 180 with the subject position data 160 and the measurements of the subject position signals 148. For example, the reference three-dimensional coordinate system 180 can comprise multiple instances of data 192 derived from the subject position data 160 by applying one or more transformation 182 to the multiple instances of data 184 of the subject position data 160. In some embodiments, the motion of the head 102 of the measurement subject 100 can be substantially removed via the reference three-dimensional coordinate system 180 being substantially static. Specifically, each of the multiple instances of data 184 of the subject position data 160 can be mapped to the reference three-dimensional coordinate system 180 according to the one or more transformation 182 that can change according to the coordinate index 194 to accommodate variation in the subject position data 160 associated with motion of the head 102 of the measurement subject 100.

Referring collectively to FIGS. 1, 2A, 2B, 3, 4 and 5, to correct from apparent spinning around the plane of the one or more subject position sensors 132, the subject position data 160 can be rotated such that the data is indicative of a fixed angle between the first subject position sensor 134 and the second subject position sensor 136 and a fixed angle between the first subject position sensor 134 and the third subject position sensor 138. In some embodiments, the subject position data 160 can be rotated such that the reference three-dimensional coordinate system 180 is indicative of the one or more subject position sensors 132 forming a plane substantially level and substantially parallel with the ground, e.g., a floor supporting the measurement subject 100.

According to the embodiments described herein, the prosthetic position data 162 can be transformed according to one or more transformation 183 prior to comparison with the reference three-dimensional coordinate system 180. In some embodiments, the one or more transformation 183 can be substantially the same as the transformation 182, which can be applied to derive the reference three-dimensional coordinate system 180 from subject position data 160. For example, the prosthetic position data 162 can be transformed to correct for apparent spinning, i.e., the transformation 182 utilized to fix the angle between the first subject position sensor 134 and the second subject position sensor 136 and the angle between the first subject position sensor 134 and the third subject position sensor 138 can be applied to the prosthetic position data 162. Alternatively or additionally, the prosthetic position data 162 can be transformed such that the prosthetic position data 162 is indicative of the one or more prosthetic tracking sensors 140 forming a plane substantially level and substantially parallel with the ground.

In some embodiments, the one or more transformation 182 can be determined first to substantially remove motion of the head 102 of the measurement subject 100 and then applied to the prosthetic position data 162 as at least a portion of the one or more transformation 183. Specifically, the coordinate index 194 of the reference three-dimensional coordinate system 180 and the prosthetic position index 190 of the prosthetic position data 162 can be utilized to link the one or more transformation 182 to the one or more transformation 183. It is noted that the transformation of each of the subject position data 160 and the prosthetic position data 162 can be applied after the conditioning of process 204. Alternatively, the transformation of each of the subject position data 160 and the prosthetic position data 162 can be applied before the conditioning of process 204.

Presentation

Referring collectively to FIGS. 1, 4 and 5, at process 208, the prosthetic position data 162 can be compared, automatically with one or more comparison processors 164, to the reference three-dimensional coordinate system 180. The comparison can occur according to a comparison order that is configured to link the prosthetic position data 162 to the reference three-dimensional coordinate system 180. Thus, if desired, the comparison order can be utilized to substantially synchronize the prosthetic position data 162 to the reference three-dimensional coordinate system 180. Specifically, in some embodiments, each of the multiple instances of data 192 of the reference three-dimensional coordinate system 180 can correspond to one of the multiple instances of data 184 of the subject position data 160. As is noted above, the multiple instances of data 192 of the reference three-dimensional coordinate system 180 can be organized according to the coordinate index 194, which can be indicative of measurements taken during movement of the head 102 of the measurement subject 100. For example, if the coordinate index 194 were time indexed, the multiple instances of data 192 of the reference three-dimensional coordinate system 180 could be organized over time corresponding to movement of the head 102 of the measurement subject 100 over time. Similarly, the prosthetic position index 190 could be time indexed with the multiple instances of data 188 of the prosthetic position data 162 changing over time corresponding to movement of the dental prosthetic 120 over time.

When the comparison order is substantially synchronized, each of the multiple instances of data 188 of the prosthetic position data 162 can be compared to one of the multiple instances of data 192 of the reference three-dimensional coordinate system 180 that corresponds to a contemporaneous measurement according to the prosthetic position index 190 and the coordinate index 194. Specifically, the reference three-dimensional coordinate system 180 can correspond to a measurement of the subject position signal 148 that occurred substantially simultaneously with a measurement of the prosthetic tracking signal 150 corresponding to the prosthetic position data 162. In some embodiments, the comparison can generate relative prosthetic position data 196 indicative of relative motion of the dental prosthetic 120 with respect to the oral cavity 104 of the measurement subject 100. The relative prosthetic position data 196 can comprise multiple instances of data 198 ordered according to a relative prosthetic position index 199. The relative prosthetic position index 199 can be encoded to link the multiple instances of data 198 of the relative prosthetic position data 196 with the subject position data 160, the prosthetic position data 162, and the reference three-dimensional coordinate system 180.

Without being bound to theory, it is believed that the prosthetic position data 162 can be indicative of movement of both the head 102 of the measurement subject 100 and movement of the dental prosthetic 120 with respect to the oral cavity 104 of the measurement subject 100. Additionally, it is believed that the subject position data 160 can be indicative of the movement of the head 102 of the measurement subject 100. Accordingly, in some embodiments, the relative motion of the dental prosthetic 120 with respect to the oral cavity 104 of the measurement subject 100 can be isolated by considering the motion of prosthetic position data 162 with respect to the reference three-dimensional coordinate system 180.

Figure 6:
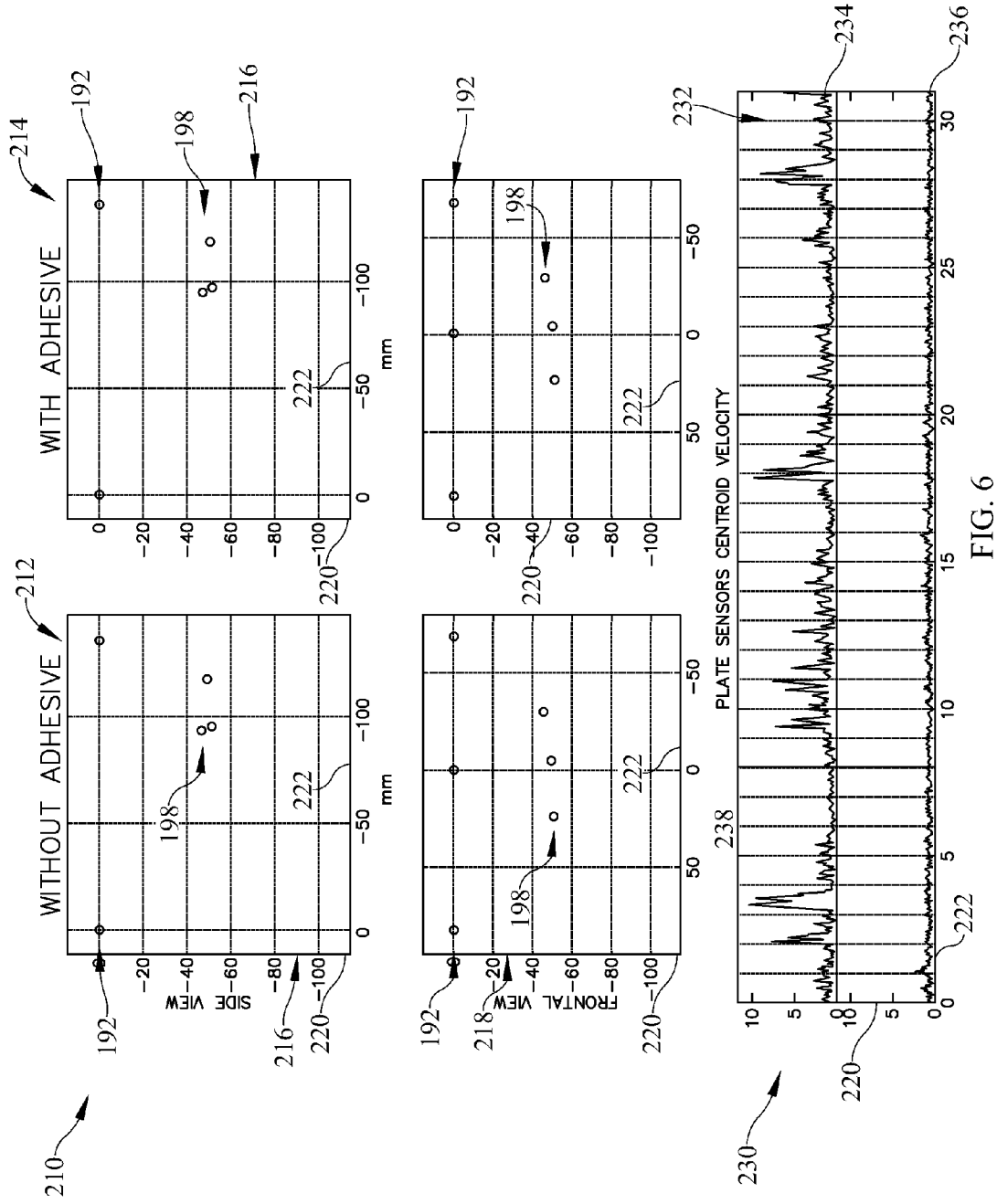
FIG. 6 schematically depicts a graphical summary for characterizing in vivo operations of dental prosthesis according to one or more embodiments shown and described herein.
Figure 7A:
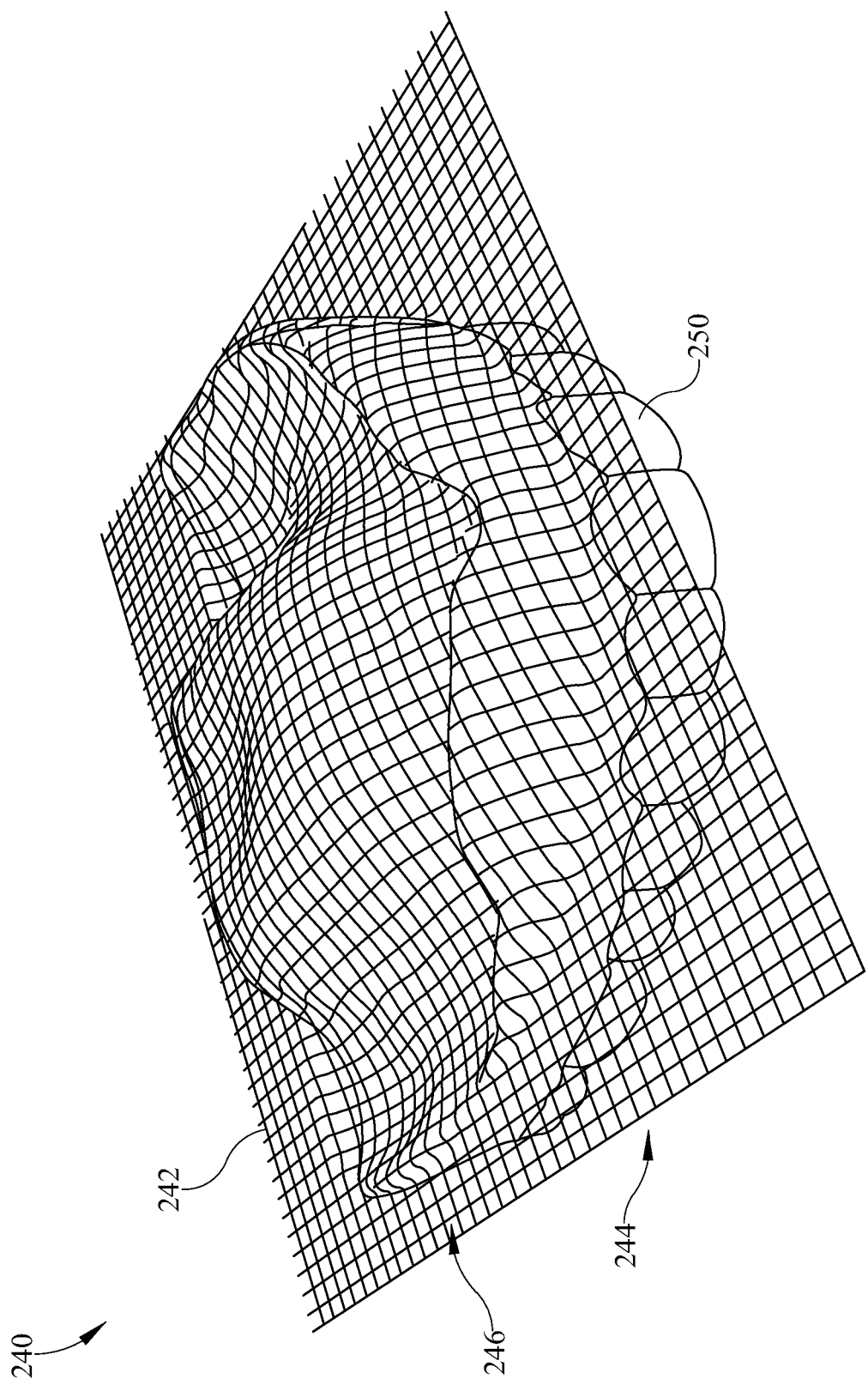
FIGS. 7A and 7B schematically depict a home position comparison for characterizing in vivo operations of dental prosthesis according to one or more embodiments shown and described herein.
Figure 7B:
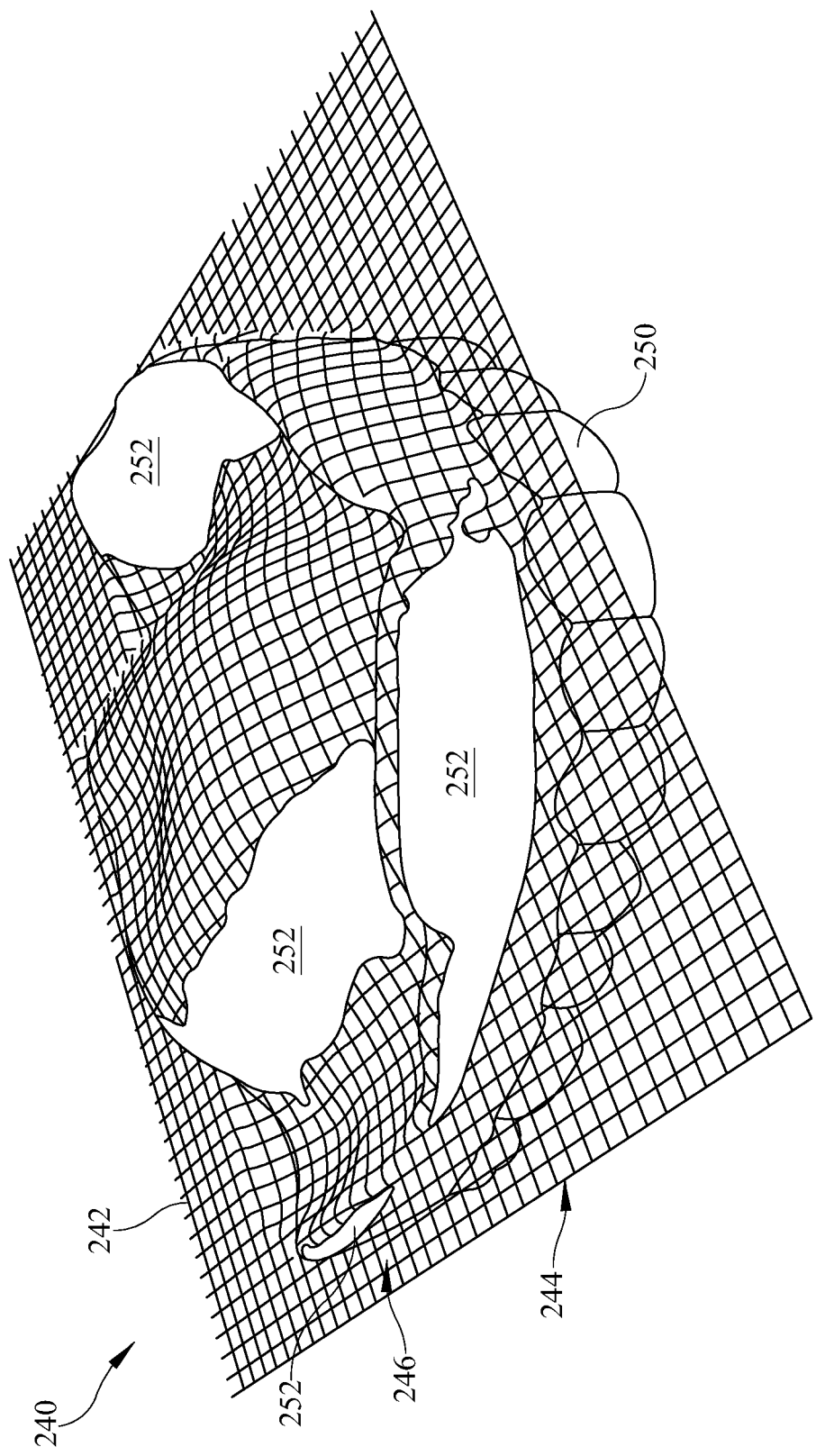

Referring collectively to FIGS. 1, 4 and 6, the reference three-dimensional coordinate system 180 and the relative prosthetic position data 196 can be presented automatically upon the display 168. For example, the one or more comparison processors 164 can execute display functions to present, upon the display 168, the reference three-dimensional coordinate system 180 and the relative prosthetic position data 196 with a graphical summary 210. In some embodiments, the graphical summary 210 can utilized to present comparisons between data sets such as, for example, replicates, different measurement subjects, different tasks consistent with typical use, different test conditions, or the like. In the embodiment depicted in FIG. 6, data collected from one or more measurement subject 100 wearing the dental prosthetic 120 without denture adhesive can be compared to data collected from one or more measurement subject 100 wearing the dental prosthetic 120 with denture adhesive.

Specifically, the graphical summary 210 can comprise a first section 212 for presenting data collected from one or more measurement subject 100 wearing the dental prosthetic 120 without denture adhesive and a second section 214 for presenting data collected from one or more measurement subject 100 wearing the dental prosthetic 120 with denture adhesive. The first section 212 and the second section 214 can each comprise a side view 216 and a frontal view 218 that are configured to present three-dimensional data. Each of the side view 216 and the frontal view 218 can comprise an ordinate axis 220 and an abscissa axis 222. In some embodiments, the ordinate axis 220 of the side view 216 can be indicative of the vertical direction of the head 102 of the measurements subject and the abscissa axis 222 can be indicative of the side of the head 102 of the measurement subject 100. The ordinate axis 220 of the frontal view 218 can be indicative of the vertical direction of the head 102 of the measurement subject 100 and the abscissa axis 222 can be indicative of the front of the head 102 of the measurement subject 100.

One or more of the multiple instances of data 192 of the reference three-dimensional coordinate system 180 derived from data collected without adhesive can be plotted on the side view 216 and the frontal view 218 of the first section 212. Additionally, one or more of the multiple instances of data 192 of the reference three-dimensional coordinate system 180 of the reference three-dimensional coordinate system 180 derived from data collected with adhesive can be plotted on the side view 216 and the frontal view 218 of the second section 214. Similarly, one or more of the multiple instances of data 198 of the relative prosthetic position data 196 derived from data collected without adhesive can be plotted on the side view 216 and the frontal view 218 of the first section 212. One or more of the multiple instances of data 198 of the relative prosthetic position data 196 derived from data collected with adhesive can be plotted on the side view 216 and the frontal view 218 of the second section 214. In embodiments where the first section 212 and the second section 214 are presented contemporaneously, the data collected without denture adhesive can be compared side-to-side with data collected with denture adhesive.

In some embodiments, the graphical summary 210 can comprise a derived data section 230 for presenting prosthetic function data 232 that is calculated based upon the relative prosthetic position data 196. The prosthetic function data 232 can be utilized to present physical information of the dental prosthetic 120 by using the relative prosthetic position data 196 as input to a mathematical function such as, for example, a first derivative of the relative prosthetic position data 196 can generate velocity information, a second derivative of the relative prosthetic position data 196 can generate acceleration information, statistical functions of the relative prosthetic position data 196 can generate summary information, etc.

The derived data section 230 can comprise an ordinate axis 220 indicative of the magnitude of the prosthetic function data 232 and an abscissa axis 222 indicative of the relative prosthetic position index 199. In some embodiments, the prosthetic function data 232 can comprise a velocity trace 234 derived from the relative prosthetic position data 196 of data collected without adhesive and a velocity trace 236 derived from the relative prosthetic position data 196 of data collected with adhesive. Each of the velocity trace 234 and the velocity trace 236 can vary with respect to the abscissa axis 222 of the derived data section 230. The velocity trace 234 and the velocity trace 236 can each be indicative of the velocity of the dental prosthetic 120. For example, the dental prosthetic 120 can be modeled as a solid body and the velocity of a centroid of the solid body can be calculated from the relative prosthetic position data 196.

The graphical summary 210 can present data statically. Alternatively or additionally, the graphical summary 210 can be configured to present data dynamically. For example, the first section 212, the second section 214, the derived data section 230, or a combination thereof can be animated. In some embodiments, animation of the first section 212, the second section 214, and the derived data section 230 can be synchronized according to the relative prosthetic position index 199. For example, the graphical summary 210 can comprise an index indicator 238 that is located within the derived data section 230. During animation, the index indicator 238 can move along the velocity trace 234, the velocity trace 236, and the abscissa axis 222 of the derived data section 230 to indicate the position of the animation with respect to the relative prosthetic position index 199. Additionally, the multiple instances of data 198 of the relative prosthetic position data 196 can update within the first section 212 and the second section 214 in accord with the position of the index indicator 238 with respect to the abscissa axis 222 of the derived data section 230. Furthermore, the coordinate index 194 can be synchronized to the relative prosthetic position index 199 such that the multiple instances of data 192 of the reference three-dimensional coordinate system 180 can update within the first section 212 and the second section 214 in accord with the position of the index indicator 238 with respect to the abscissa axis 222 of the derived data section 230.

Comparison Information

Referring collectively to FIGS. 1, 4, 7A and 7B, a home position can be derived from the relative prosthetic position data 196. The home position can be utilized as a basis for determining comparison information. Accordingly, the home position can comprise coordinates indicative of a neutral or ideal location of the dental prosthetic 120 with respect to the oral cavity 104 of the measurement subject 100. In some embodiments, the home position can be derived from the relative prosthetic position data 196 that corresponds to rest position data. For example, the home position can be calculated using a statistic of the rest position data such as, for example, the mean, the median, or the like. Specifically, in one embodiment, the home position can be determined by taking the median of all of the rest position data collected from the measurement subject 100 during a single testing instance.

Once the home position is determined, comparison information can be calculated from the relative prosthetic position data 196 corresponding to data collected while the measurement subject 100 performed the one or more tasks consistent with typical use. The comparison information can comprise a distance from home or a statistic derived from the distance from home. In some embodiments, the distance from home can be a measurement of the distance between one of the multiple instances of data 198 of the relative prosthetic position data 196 and the home position such as, for example, Euclidean distance or the like. Accordingly, the distance from home can be calculated for the multiple instances of data 198 of the relative prosthetic position data 196 to generate a plurality of distance from home instances. The distance from home instances can be segregated based upon any of the identifiers noted herein such as, for example, task consistent with typical use, denture adhesive type, no denture adhesive, measurement subject, or the like. Furthermore, the segregated or non-segregated plurality of distance from home instances can be summarized using statistics such as, for example, mean distance from home, median distance from home, proportion of distance from home instances above or below a predetermined length (e.g., 1 millimeters in one embodiment, 1.5 millimeters in another embodiment, or 2 millimeters in another embodiment), total distance from home, minimum distance from home, maximum distance from home, or the like. Moreover, when the relative prosthetic position data 196 can be associated with time, the statistics can include, mean time from home, proportion of moments of time from home above or below a predetermined length (e.g., 1 millimeters in one embodiment, 1.5 millimeters in another embodiment, or 2 millimeters in another embodiment), total time from home, or the like Accordingly, the distance from home can provide an objective measurement for characterizing and comparing the in vivo operation of the dental prosthetic 120.

In some embodiments, a home position comparison 240 can be presented automatically upon the display 168. The home position comparison 240 can be configured to present information indicative of movement of the dental prosthetic 120 within the oral cavity 104 of the measurement subject 100. The home position comparison 240 can comprise a home position object 242 indicative of the home position of the dental prosthetic 120 and a dental prosthetic object 250 indicative of the dimensions of the dental prosthetic 120. Specifically, the dental prosthetic object 250 can be a model of the dental prosthetic 120 that is scaled to the home position object 242. As is noted above, the dental prosthetic 120 can be formed to match the topography of the oral cavity 104. Accordingly, the retention surface 124 of the dental prosthetic 120 can serve as an analog to the topography of the oral cavity 104 of the measurement subject.

In some embodiments, the home position object 242 can be shaped to match the retention surface 124 of the dental prosthetic 120, when the dental prosthetic 120 is positioned in the home position. Accordingly, the home position object 242 can be indicative of the topography of the oral cavity 104 when the dental prosthetic 120 is in the home position. The home position object 242 can operate as a boundary between an oral cavity side 244 of the home position comparison 240 and a compression side 246 of the home position comparison 240. The oral cavity side 244 can be indicative of the volume contained by the oral cavity 104, i.e., when an object is on the oral cavity side 244 of the home position object 242, the home position comparison 240 is indicative of the object being within the volume contained by the oral cavity 104. The compression side 246 can be indicative of the topography of the oral cavity 104, i.e., when an object is on the compression side 246 of the home position object 242, the home position comparison 240 is indicative of the object being exerting a compressive force upon the topography of the oral cavity 104 (e.g., a deflection).

Referring collectively to FIGS. 1, 4, 7A and 7B, the home position comparison 240 can be utilized to show the relative prosthetic position data 196 with respect to the home position. Specifically, the dental prosthetic object 250 can be placed within the home position comparison 240 at a position that corresponds to one of the multiple instances of data 198 of the relative prosthetic position data 196. In some embodiments, the relative prosthetic position data 196 can indicate that the dental prosthetic 120 is pressing upon the topography of the oral cavity 104. Specifically, the dental prosthetic object 250 can comprise one or more deflecting portions 252 that extend beyond the home position object 242 and into the compression side 246 of the home position comparison 240. Accordingly, the one or more deflecting portions 252 of the dental prosthetic object 250 can correspond to the portions of the dental prosthetic 120 that compress or exert pressure upon the topography of the oral cavity 104. The home position comparison 240 can statically present the dental prosthetic object 250 with respect to the home position object 242, i.e., a single position that corresponds to one of the multiple instances of data 198 of the relative prosthetic position data 196. Alternatively or additionally, the home position comparison 240 can dynamically present the dental prosthetic object 250 with respect to the home position object 242, i.e., animation of a sequence of positions that correspond to the multiple instances of data 198 of the relative prosthetic position data 196.

It should now be understood that the embodiments described herein can be utilized to characterize the in vivo operation of dental prosthesis. Accordingly, the position, movement, and relative movement of dental prosthesis can be characterized into objective data. The objective data can be correlated with the properties of denture adhesive to evaluate the functionality and efficacy of the denture adhesive. For example, the denture adhesive can be characterized according to adhesion, which can characterize the ability of the denture adhesive to hold dentures to an oral cavity, and cohesion, which can characterize the ability of the denture adhesive to hold together. Thus, the embodiments described herein can be utilized to provide additional feedback that can be used to screen improved product formulations.

Moreover, the embodiments described herein can be utilized to communicate the objective measurements of in vivo operation of dental prosthesis as compelling demonstrations and full-motion models for consumers and dental professionals. Accordingly, the objective measures can be communicated to consumers to demonstrate the relative benefits of different types of denture adhesive, dental prosthesis, of combinations thereof. Dental professionals can also make use of such models to add additional feedback to promote improvements to the fit of the dental prosthesis.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for characterizing in vivo operation of a dental prosthetic, the method comprising:
    attaching one or more subject position sensors to a measurement subject;
    transmitting subject position signals by one or more subject position sensors attached to the measurement subject;
    deriving subject position data from subject position signals,
    wherein the subject position data is ordered according to a subject position index;
    attaching one or more prosthetic tracking sensors to a dental prosthetic located within an oral cavity of the measurement subject;
    transmitting prosthetic tracking signals from the one or more prosthetic tracking sensors;
    deriving prosthetic positioning data from the prosthetic tracking signals,
    wherein the one or more prosthetic tracking sensors are non-line-of-sight sensors, and wherein the prosthetic tracking signals and the subject position signals are transmitted contemporaneously, and wherein the prosthetic position data is ordered according to a prosthetic position index;
    transforming the subject position data into a reference three-dimensional coordinate system, wherein the reference three-dimensional coordinate system is ordered according to a coordinate index, and wherein the coordinate index is based at least in part upon the subject position index; and comparing, automatically with one or more processors, the prosthetic position data and the reference three-dimensional coordinate system according to a comparison order to characterize the dental prosthetic, wherein the comparison order is based at least in part upon the prosthetic position index and the coordinate index.

2. The method of claim 1, further comprising:
smoothing the subject position data and the prosthetic position data.

3. The method of claim 1, wherein:
the subject position data is transformed into the reference three-dimensional coordinate system, such that the reference three-dimensional coordinate system is indicative of the one or more subject position sensors forming a level plane.

4. The method of claim 1, further comprising:
transforming the prosthetic position data whereby the prosthetic position data is indicative of the one or more prosthetic tracking sensors forming a level plane.

5. The method of claim 1, further comprising:
generating relative prosthetic position data indicative of relative motion of the dental prosthetic with respect to the oral cavity of the measurement subject from a comparison between the prosthetic position data and the reference three-dimensional coordinate system.

6. The method of claim 5, further comprising:
deriving a home position from the relative prosthetic position data, wherein the home position is indicative of a neutral position of the dental prosthetic.

7. The method of claim 6, further comprising:
calculating a distance from home indicative of a distance from one or more instance of the relative prosthetic position data and the home position, collecting the prosthetic tracking signals while the measurement subject performs one or more tasks consistent with typical use, and wherein the one or more instance of the relative prosthetic position data corresponds to the prosthetic tracking signals collected while the measurement subject is performing the one or more tasks consistent with typical use.

8. The method of claim 7, further comprising deriving a statistic from the distance from home.

9. The method of claim 8, wherein the statistic comprises a mean, a median, a proportion of the distance from home above or below a predetermined length, a total distance, a minimum, or a maximum.

10. The method of claim 8, wherein the statistic comprises a time from home, a proportion of moments of time the distance from home is above or below a predetermined length, or a total time from home.

11. The method of claim 6, further comprising:
presenting a home position comparison upon a display, wherein the home position comparison comprises a home position object indicative of the home position and a dental prosthetic object indicative of dimensions of the dental prosthetic, and wherein dental prosthetic object is placed in a position with respect to the home position object that corresponds to one or more instance of the relative prosthetic position data.

12. The method of claim 11, wherein the home position object is shaped to match a retention surface of the dental prosthetic.

13. The method of claim 11, wherein the home position object is presented dynamically.

14. The method of claim 5, further comprising:
presenting a graphical summary upon a display, wherein the graphical summary comprises the relative prosthetic position data and the reference three-dimensional coordinate system.

15. The method of claim 14, wherein the graphical summary comprises compared data sets.

16. The method of claim 14, wherein the graphical summary is presented dynamically.

17. The method of claim 5, further comprising:
presenting prosthetic function data upon a display, wherein the prosthetic function data is calculated based upon the relative prosthetic position data.

18. The method of claim 17, wherein the prosthetic function data comprises velocity information or acceleration information.

19. The method of claim 1, further comprising:
attaching one of the one or more subject position sensors directly to a head of the measurement subject.

20. The method of claim 19, wherein the one of the one or more subject position sensors is attached to a bridge of a nose of the measurement subject.

21. The method of claim 19, wherein the one of the one or more subject position sensors is attached at a left mastoid or a right mastoid of the measurement subject.

22. The method of claim 1, wherein the one or more prosthetic tracking sensors are embedded within the dental prosthetic.

23. The method of claim 1, wherein:
the one or more subject position sensors comprises three subject position sensors that define a first triangular pattern;
the one or more prosthetic tracking sensors comprises three prosthetic tracking sensors that define a second triangular pattern; and
the first triangular pattern has a larger perimeter than the second triangular pattern.

24. A method for characterizing in vivo operation of a dental prosthetic, the method comprising:
attaching one or more subject position sensors to a measurement subject;
transmitting subject position signals by one or more subject position sensors attached to the measurement subject;
deriving subject position data from subject position signals,
wherein the subject position data is ordered according to a subject position index;
attaching one or more prosthetic tracking sensors to a dental prosthetic located within an oral cavity of the measurement subject;
transmitting prosthetic tracking signals from the one or more prosthetic tracking sensors;
deriving prosthetic positioning data from the prosthetic tracking signals,
wherein the one or more prosthetic tracking sensors are reactive to an excitation field, and wherein the prosthetic position data is ordered according to a prosthetic position index;
transforming the subject position data into a reference three-dimensional coordinate system, wherein the reference three-dimensional coordinate system is ordered according to a coordinate index, and wherein the coordinate index is based at least in part upon the subject position index; and
comparing, automatically with one or more processors, the prosthetic position data and the reference three-dimensional coordinate system according to a comparison order to characterize the dental prosthetic, wherein the comparison order is based at least in part upon the prosthetic position index and the coordinate index.

* * * * *